(12) United States Patent
Eisinger (10) Patent No.: US 11,717,322 B2
(45) Date of Patent: Aug. 8, 2023

(54) FLEXIBLE CANNULA HAVING SELECTIVE RIGIDITY

(71) Applicant: Covidien LP, Mansfield, MA (US)

(72) Inventor: Joseph Eisinger, Northford, CT (US)

(73) Assignee: Covidien LP, Mansfield, MA (US)

(*) Notice: Subject to any disclaimer, the term of this patent is extended or adjusted under 35 U.S.C. 154(b) by 354 days.

(21) Appl. No.: 16/994,750

(22) Filed: Aug. 17, 2020

(65) Prior Publication Data
US 2022/0047300 A1    Feb. 17, 2022

(51) Int. Cl.
*A61B 17/34* (2006.01)
(52) U.S. Cl.
CPC ...... *A61B 17/3431* (2013.01); *A61B 17/3423* (2013.01); *A61B 17/3498* (2013.01)
(58) Field of Classification Search
CPC ............ A61B 17/3431; A61B 17/3423; A61B 17/3498; A61B 17/3421; A61B 17/3417; A61B 2017/00566; A61B 17/3415; A61B 17/3462; A61B 2017/00292; A61B 17/3478; A61B 1/018; A61B 17/0218; A61B 2017/00535
See application file for complete search history.

(56) References Cited

U.S. PATENT DOCUMENTS

| 397,060 A | 1/1889 | Knapp |
|---|---|---|
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |

(Continued)

FOREIGN PATENT DOCUMENTS

| EP | 0480653 A1 | 4/1992 |
|---|---|---|
| EP | 0610099 A2 | 8/1994 |

(Continued)

OTHER PUBLICATIONS

Extended European Search Report dated Dec. 16, 2021 issued in corresponding EP Appln. No. 21191438.7.

*Primary Examiner* — Katherine M Shi
*Assistant Examiner* — Nasheha Baset
(74) *Attorney, Agent, or Firm* — Carter, DeLuca & Farrell LLP (57) ABSTRACT

A surgical access device includes a housing having a tubular member extending therefrom. The tubular member has inner and outer walls defining an annular lumen therebetween. A passageway extends between proximal and distal openings of the tubular member. The passageway is configured to receive a surgical instrument therethrough. A conduit is disposed in the annular lumen and includes spiral segments where each spiral segment is engaged with an adjacent spiral segment. The conduit is flexible in a first state and is fixed in a second state. A valve assembly is coupled to the housing and includes a port that is in fluid communication with the annular lumen. The port is attachable to a source of fluid.

19 Claims, 6 Drawing Sheets

(56) References Cited

U.S. PATENT DOCUMENTS

| | | |
|---|---|---|
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,337,733 A | 8/1994 | Bauerfeind et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,454,645 B1 | 9/2002 | Baba et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 2008/0091170 A1 | 4/2008 | Vargas et al. |
| 2013/0289478 A1* | 10/2013 | Kim .............. A61B 1/00078 604/95.04 |
| 2015/0038793 A1* | 2/2015 | Prior .............. A61M 5/329 600/204 |

(56) References Cited

U.S. PATENT DOCUMENTS

2015/0216589 A1     8/2015    Wittenberger et al.
2019/0321591 A1    10/2019    Rogers
2020/0178763 A1     6/2020    Tilson et al.

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2018022813 A1 | 2/2018 |
| WO | 2020018934 A1 | 1/2020 |

* cited by examiner

FLEXIBLE CANNULA HAVING SELECTIVE RIGIDITY

FIELD

The present disclosure generally relates to surgical instruments for minimally invasive surgery. In particular, the present disclosure relates to a flexible cannula having selective rigidity.

BACKGROUND

A minimally invasive surgical procedure is one in which a surgeon enters a patient's body through one or more small openings in the patient's skin or naturally occurring openings (e.g., mouth, anus, or vagina). As compared with traditional open surgeries, minimally invasive surgical procedures have several advantages and disadvantages. Minimally invasive surgeries include arthroscopic, endoscopic, laparoscopic, and thoracoscopic surgeries. In laparoscopic and endoscopic surgical procedures, a small incision or puncture is made in a patient's body (e.g., abdomen) to provide an entry point for a surgical access device which is inserted into the incision and facilitates the insertion of instruments used in performing surgical procedures within an internal surgical site. Minimally invasive surgical procedures are advantageous in that, as compared to traditional open surgical procedures, both trauma to the patient and recovery time are reduced due to the relatively small incisions formed through the patient's body. However, since these access incisions are small, only elongated, small diametered instrumentation may be used to access the internal body cavities and organs.

During such procedures, surgical objects such as surgical access devices (e.g., cannulae) are inserted into the patient's body through the incision in tissue. In general, prior to the introduction of the surgical object into the patient's body, insufflation gases are used to enlarge the area surrounding the target surgical site to create a larger, more accessible work area. The surgeon is then able to perform the procedure within the abdominal cavity by manipulating the instruments that have been extended through the access devices. The manipulation of such instruments within the internal body is similarly limited by both spatial constraints and the need to maintain the body cavity in an insufflated state.

SUMMARY

A surgical access device includes a housing and a tubular member extending from the housing. The tubular member has proximal and distal openings and includes an outer wall and an inner wall that define an annular lumen therebetween. A passageway extends between the proximal and distal openings and is configured to receive a surgical instrument therethrough. A conduit extends along a length of the tubular member and is disposed in the annular lumen. The conduit is transitionable between first and second states. The conduit includes spiral segments, where each spiral segment is engaged with an adjacent spiral segment such that the conduit has a flexible configuration in the first state and a fixed configuration in the second state. A valve assembly is coupled to the housing and includes a port that is in fluid communication with the annular lumen and attachable to a source of fluid.

In an aspect, a fluid may be disposed in the annular lumen.

In another aspect, the conduit may transition to the first state in the presence of fluid in the annular lumen.

In a further aspect, the conduit may transition to the second state in the absence of the fluid in the annular lumen.

In another aspect, each spiral segment may have first and second portions where each of the first and second portions may have a generally C-shaped cross-sectional configuration.

In aspects, the first portion of each spiral segment may be slidable with respect to the second portion of the adjacent spiral segment such that the conduit is in the first state.

In an aspect, the first portion of each spiral segment may be fixed with respect to the second portion of the adjacent spiral segment such that the conduit is in the second state.

In another aspect, the tubular member may be flexible and adapted to receive a flexible surgical instrument therein.

In aspects, the inner and outer walls of the annular lumen may contact surfaces of the spiral segments of the conduit.

A method of accessing a surgical site includes positioning a tubular member of a surgical access device through an opening in tissue, guiding a distal portion of the tubular member toward a target site, manipulating the tubular member to follow a predetermined path while the tubular member is in a first state, and removing fluid from an annular lumen defined between inner and outer walls of the tubular member thereby transitioning the tubular member from the first state to a second state wherein the tubular member is rigid.

In an aspect, manipulating the tubular member may include manipulating a conduit disposed in the annular lumen of the tubular member.

In another aspect, manipulating the conduit may include manipulating spiral segments of the conduit such that a first section of one spiral segment slidably engages a second section of an adjacent spiral section.

In a further aspect, removing fluid from the annular lumen may cause the inner and outer walls of the lumen to contact surfaces of the spiral segments of the conduit.

In yet another aspect, removing fluid from the annular lumen may cause first sections of spiral segments of a conduit disposed in the annular lumen to become fixed in relation to second sections of adjacent spiral segments of the conduit thereby defining the second state of the tubular member.

In an aspect, the method may include inserting a flexible surgical instrument through the tubular member while the tubular member is in the first state.

In a further aspect, removing fluid from the annular lumen may include operating a valve on a housing that is coupled to a proximal end of the tubular member.

In yet another aspect, the method may include introducing fluid into the annular lumen thereby transitioning the tubular member from the second state to the first state and may include removing the tubular member from the opening in tissue.

In one aspect, introducing fluid into the annular lumen may include operating a valve on a housing that is coupled to a proximal end of the tubular member.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings.

Figure 1:
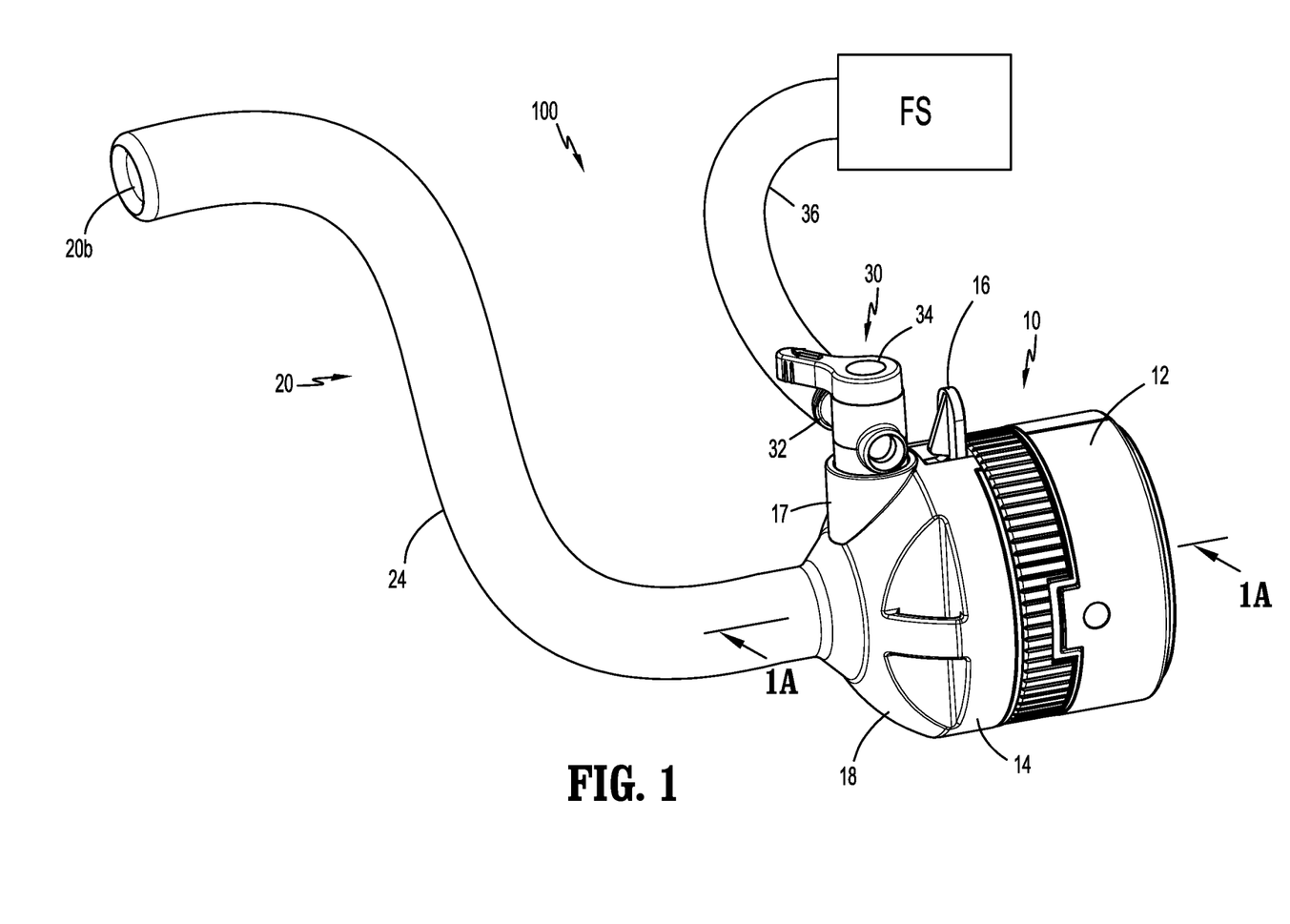
FIG. 1 is a perspective view of a surgical access device with a housing and a tubular member in a first state according to an aspect of the present disclosure.
Figure 1A:
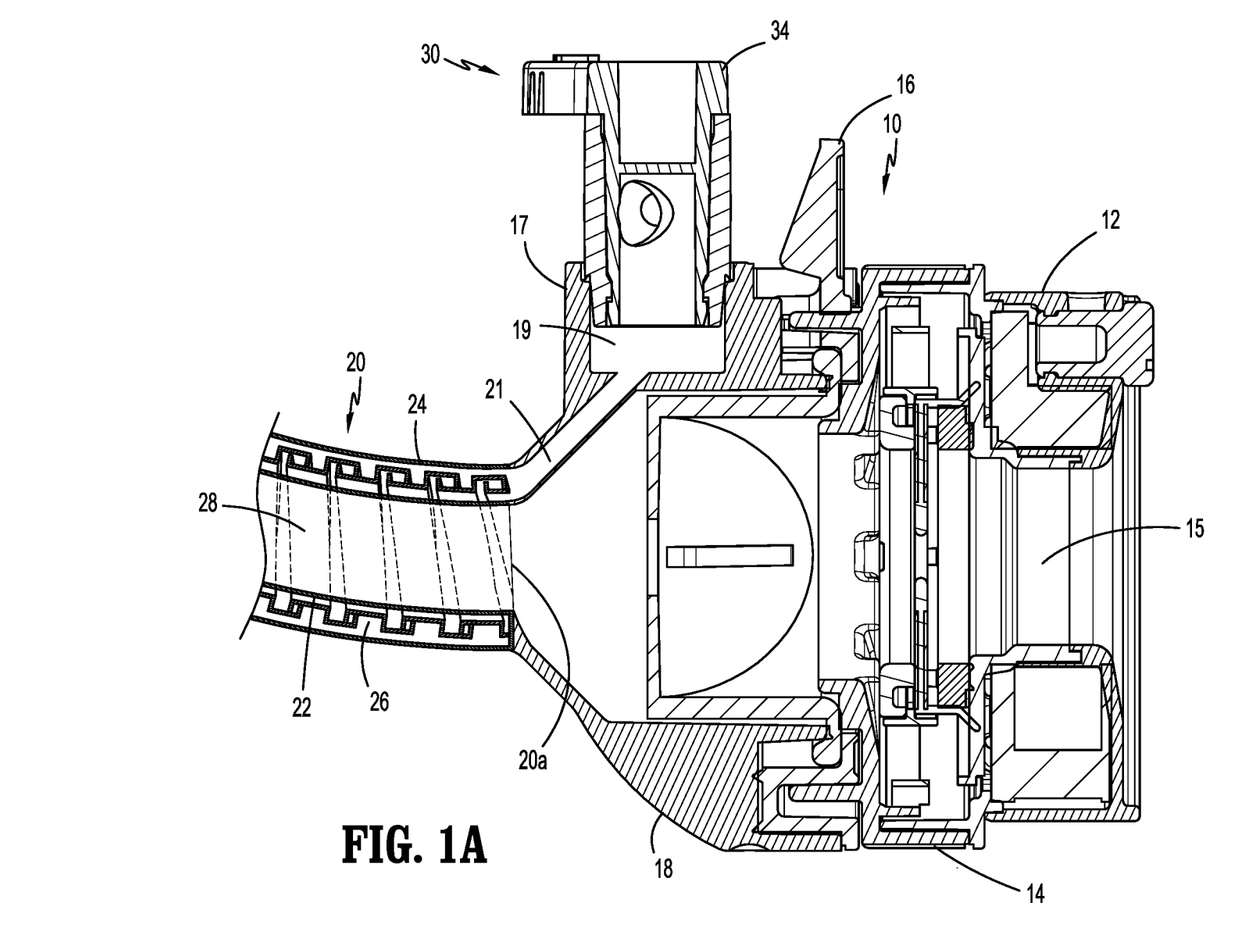
FIG. 1A is a cross-sectional view of the housing and a proximal region of the tubular member taken along section line 1A-1A of FIG. 1.

With initial reference to FIGS. 1 and 1A, a surgical access device according to the present disclosure is illustrated and identified as surgical access device 100. Surgical access device 100 has a housing 10 and a tubular member 20 extending therefrom. The tubular member 20 is an elongate structure that is formed from a suitable biocompatible polymeric material (e.g., silicone rubber or ethylene propylene diene monomer (EPDM) rubber) with proximal and distal openings 20a, 20b defining a passageway 28 extending therebetween. The polymeric material used for the tubular member 20 allows the tubular member 20 to be flexible in a number of directions thereby allowing numerous configurations of the tubular member 20. The housing 10 includes an upper housing 12 releasably coupled to a lower housing 14. A tab 16 extends radially from the lower housing 14 and is actuable to allow relative rotation between the upper and lower housings 12, 14. The relative rotation between the upper and lower housings 12, 14 allows the upper and lower housings 12, 14 to be coupled together or separated from one another. The lower housing 14 has a frusto-conical region 18 and the tubular member 20 extends therefrom. A valve assembly 30 extends laterally from the frusto-conical region 18 and is attachable to a source of fluid "FS" via a flexible tube 36. The housing 10 has a channel 15 extending therethrough that is coaxial with the proximal opening 20a of the tubular member 20. Examples of suitable housings are disclosed in commonly owned U.S. Pat. No. 10,022,149 to Holsten et al. and U.S. Patent Application Publication No. 2015/0031958 to Kleyman, the contents of which are incorporated by reference herein in their entirety.

The source of fluid "FS" may provide pressurized fluid to an annular lumen 26 of the tubular member 20 and/or may provide a vacuum to the annular lumen 26 of the tubular member 20. With brief reference to FIG. 5, the annular lumen 26 is defined between an outer wall 24, and an inner wall 22 of the tubular member. Fluid is introduced or evacuated from the annular lumen 26 through the valve assembly 30. The valve assembly 30 includes a port 32 and a valve 34 such as a stopcock valve. The open position of the valve 34 allows fluid to flow between the annular lumen 26 and the port 32 while the closed position of the valve 34 isolates the port 32 from the annular lumen 26. The valve assembly 30 is fitted into a receiver 17 in the frusto-conical region 18 of the lower housing 14 thereby defining a chamber 19 between a bottom surface of the valve assembly 30 and a bottom surface of the receiver 17. The annular lumen 26 of the tubular member 20 is fluidly coupled to the chamber 19 of the receiver 17 via a tunnel 21. With this arrangement, opening the valve 34 allows fluid to flow into or out of the annular lumen 26. Likewise, closing the valve 34 inhibits fluid flow into or out of the annular lumen 26.

Figures 2, 3:
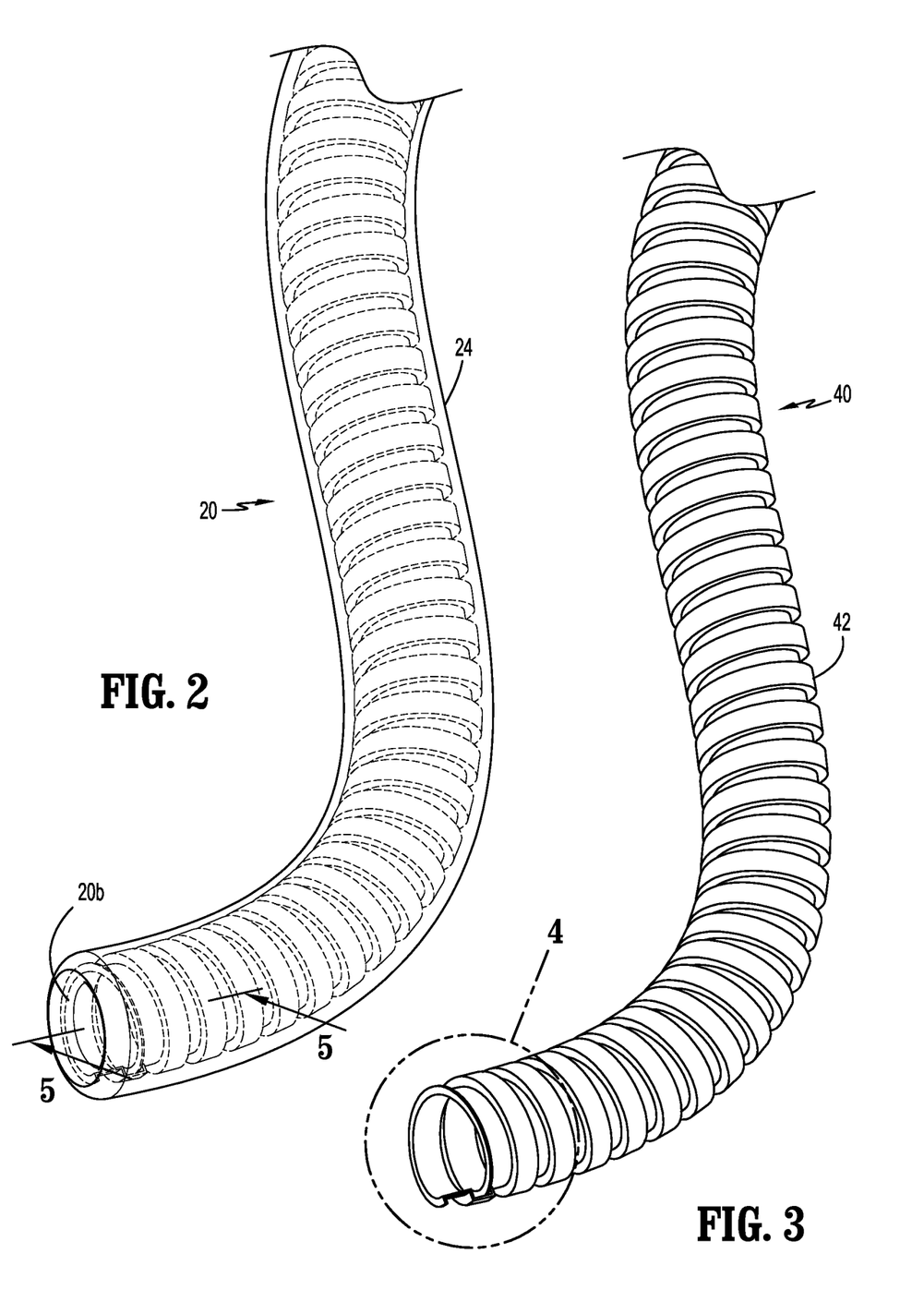
FIG. 2 is a perspective view of a distal portion of the tubular member of the surgical access device of FIG. 1 showing a conduit in phantom.
FIG. 3 is a perspective view of the conduit of FIG. 2.
Figure 4:
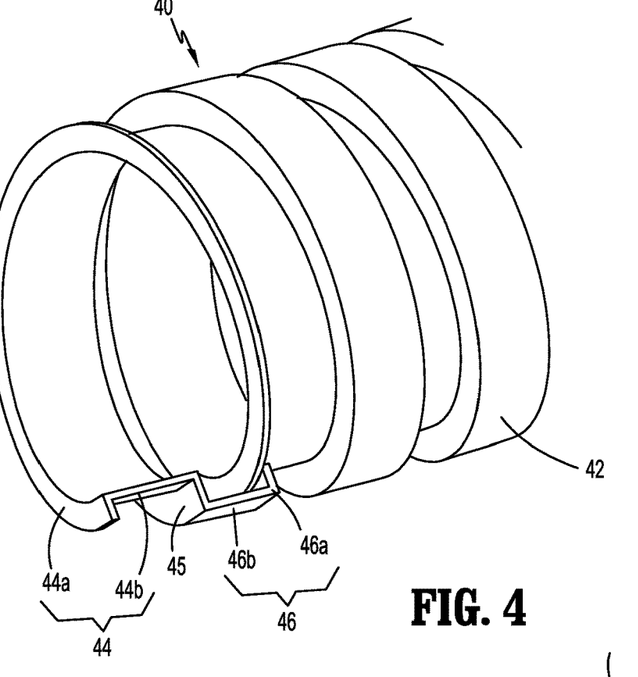
FIG. 4 is an enlarged view of the area of detail shown in FIG. 3.

Referring now to FIG. 2, a portion of the tubular member 20 is shown in a first state. A strip-wound hose or conduit 40 is disposed in the tubular member 20. The conduit 40 is formed from a biocompatible metal (e.g., stainless steel). As seen in FIGS. 3 and 4, the conduit 40 includes interlocking spiral segments 42 that are helically wound between the proximal and distal openings 20a, 20b of the tubular member 20. Each spiral segment 42 includes a first portion 44 and a second portion 46. With additional reference to FIG. 5, the first portion 44 of each spiral segment 42 includes a first flange 44a and a first trough 44b, and the second portion 46 of each spiral segment 42 includes a second flange 46a and a second trough 46b. A partition 45 connects the first and second troughs 44b, 46b and extends orthogonally to the first and second troughs 44b, 46b. As such, a cross-sectional view of the spiral segments 42 has a square wave pattern. The first flange 44a is slidably disposed in the second trough 46b and the second flange 46a is slidably disposed in the first trough 44b. In the first state of the tubular member 20, the spiral segments 42 of the conduit 40 are free to move relative to one another. As such, when manipulated by the surgeon, the first flanges 44a slide in the second troughs 46b and the second flanges 46a slide in the first troughs 44b allowing the surgeon to manipulate the tubular member 20 and the conduit 40 to achieve a particular orientation that follows a desired path through body tissue.

Figure 5:
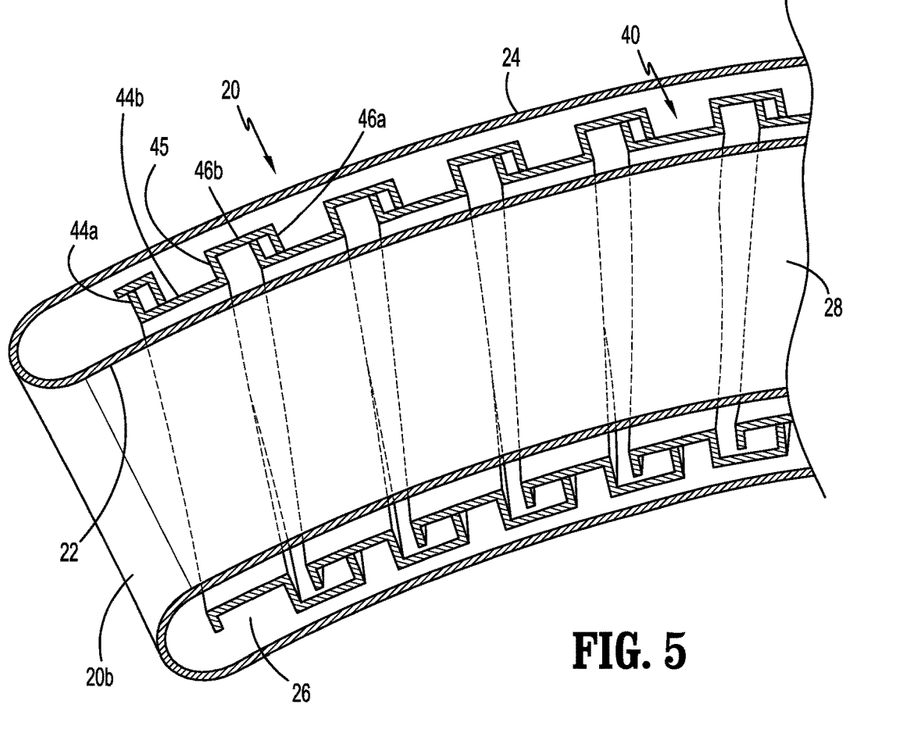
FIG. 5 is a side cross-sectional view of a distal portion of the tubular member taken along section line 5-5 of FIG. 2.

With reference to FIG. 5, and as noted above, the inner wall 22 and the outer wall 24 of the tubular member 20 define the annular lumen 26 therebetween. The annular lumen 26 extends from a proximal end of the tubular member 20 to a distal end of the tubular member 20. The annular lumen 26 has a closed distal end. When the valve 34 of the valve assembly 30 is in the closed configuration, the annular lumen 26 has a fluid-tight configuration. The conduit 40 is disposed in the annular lumen 26. When the annular lumen 26 is filled with fluid (e.g., sterile saline, $CO_2$, or air), the inner and outer walls 22, 24 move away from one another defining a gap between the conduit 40 and the inner and outer walls 22, 24. In this flexible configuration (i.e., the first state), the tubular member 20, including the conduit 40, has multiple degrees of freedom and can be flexed and articulated into a variety configurations allowing the tubular member 20 to follow a desired path through tissue to reach a target site.

Figure 6:
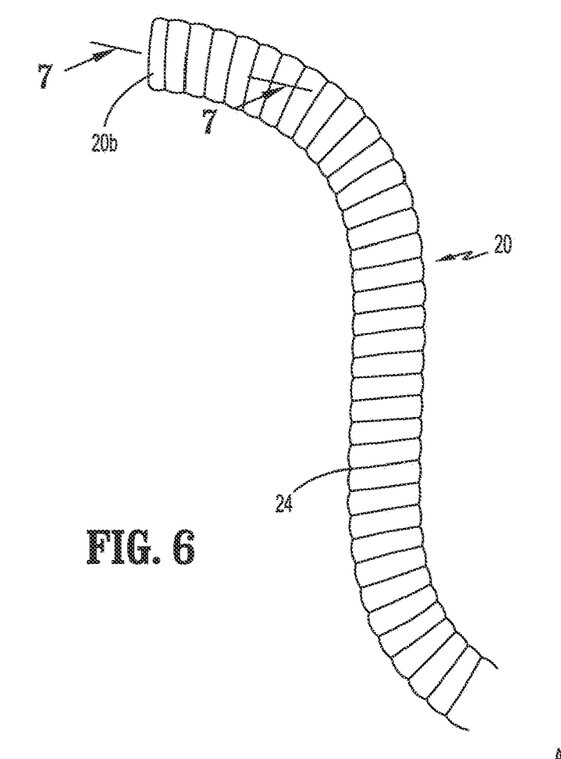
FIG. 6 is a side view of the tubular member of the surgical access device of FIG. 1 in a second state.
Figure 7:
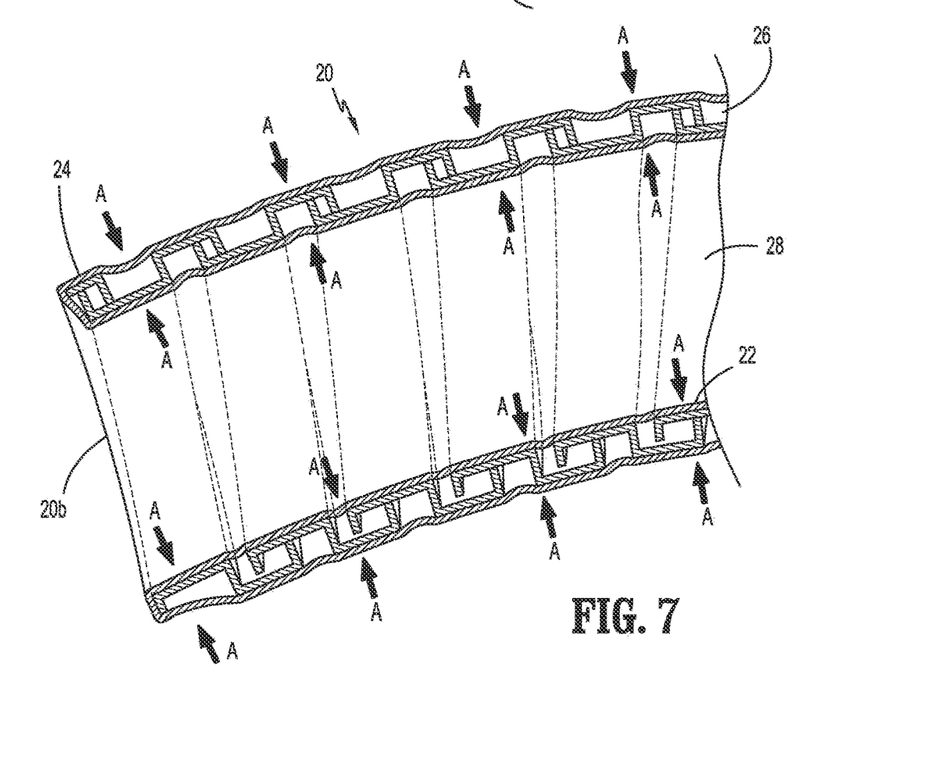
FIG. 7 is a side cross-sectional view taken along section line 7-7 of FIG. 6.

With reference now to FIGS. 6 and 7, a second state of the tubular member 20 is illustrated. By evacuating or removing the fluid in the annular lumen 26, the inner and outer walls 22, 24 that define the annular lumen 26 move towards one another in the direction of arrows "A" and squeeze the conduit 40 between the inner and outer walls 22, 24 thereby eliminating the gaps between the conduit 40 and the inner and outer walls 22, 24. By squeezing the spiral segments 42 of the conduit 40 between the inner and outer walls 22, 24 of the annular lumen 26, the flanges 44a, 46a frictionally engage the troughs 44b, 46b. In particular, the first flanges 44a frictionally engage the second troughs 46b and the second flanges 46a frictionally engage the first troughs 44b. As such, each spiral segment 42 of the conduit 40 is fixed relative to an adjacent spiral segment 42 of the conduit 40. This arrangement fixes or secures the conduit 40 and thus the tubular member 20 in a specific orientation.

Figure 8:
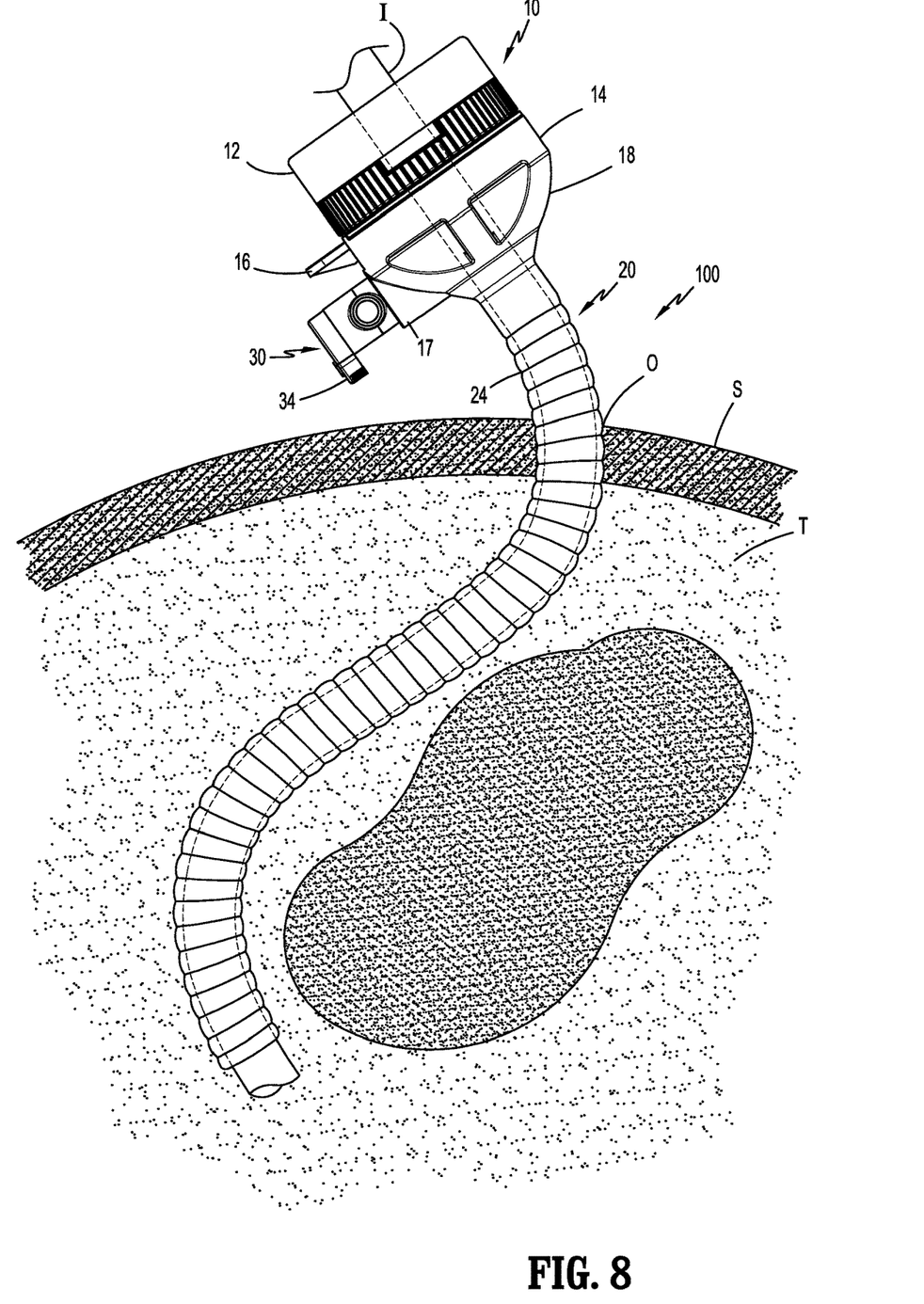
FIG. 8 is a side view of the surgical access device of FIG. 1 inserted into tissue with the tubular member in the second state.

In contrast to the flexible state (i.e., the first state) of the tubular member 20 shown in FIG. 1, the fixed state (i.e., the second state) of the tubular member 20 is shown in FIG. 8. Specifically, the tubular member 20 in the second state maintains a desired path through body tissue "T". This fixed path through tissue allows a flexible surgical instrument "I" to be inserted through the housing 10 and follow the second state of the tubular member 20 to a target site without deviating from the selected path.

In use, a surgeon inserts the tubular member 20 in the flexible or first state (FIG. 1) through an opening "O" in a patient's skin "S" (FIG. 8). The surgeon then maneuvers the tubular member 20 through tissue "T" to reach the target site. As the tubular member 20 is flexible in the first state, the surgeon is able to maneuver the tubular member 20 as needed to reach the target site even if the target site is occluded or obstructed by other structures in the body. Once the distal end of the tubular member 20 reaches the target site, the surgeon evacuates fluid from the annular lumen 26 causing the inner and outer walls 22, 24 of the tubular member 20 to compress against the spiral segments 42 of the conduit 40 transitioning the tubular member 20 to the fixed or second state (FIG. 7). In the second state, the frictional engagement between the flanges 44a, 46a and the troughs 44b, 46b of the spiral segments 42 maintains the configuration of the conduit 40 (FIG. 7). As the conduit 40 is disposed in the annular lumen 26 of the tubular member 20, the tubular member 20 also maintains the same configuration. This allows the surgeon to insert the flexible surgical instrument "I" through the housing 10 and the tubular member 20 and access the target site with the flexible surgical instrument "I" (FIG. 8).

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical access device comprising:
a housing;
a tubular member extending from the housing, the tubular member having a proximal opening and a distal opening, the tubular member including an outer wall and an inner wall defining an annular lumen;
a conduit including a passageway extending between the proximal opening and the distal opening, the passageway configured to receive a surgical instrument, wherein the conduit extends along a length of the tubular member, the conduit disposed in the annular lumen and transitionable between a first state and a second state, the conduit including a plurality of spiral segments, each spiral segment of the plurality of spiral segments having a first portion and a second portion, the first portion including a first flange and a first trough, the second portion including a second flange and a second trough, the first flange being slidably disposed in the second trough and the second flange being slidably disposed in the first trough such that each spiral segment of the plurality of spiral segments is movable relative to an adjacent spiral segment of the plurality of spiral segments such that the conduit has a flexible configuration in the first state and a fixed configuration in the second state; and
a valve assembly coupled to the housing and including a port, the port in fluid communication with the annular lumen and attachable to a source of fluid.

2. The surgical access device of claim 1, further including a fluid disposed in the annular lumen.

3. The surgical access device of claim 2, wherein the conduit transitions to the first state in the presence of fluid in the annular lumen.

4. The surgical access device of claim 3, wherein the tubular member is flexible and adapted to receive a flexible surgical instrument.

5. The surgical access device of claim 2, wherein the conduit transitions to the second state in the absence of the fluid in the annular lumen.

6. The surgical access device of claim 5, wherein the inner wall and the outer wall of the annular lumen contact surfaces of the spiral segments of the conduit.

7. The surgical access device of claim 1, wherein each first portion and each second portion has a generally C-shaped cross-sectional configuration.

8. The surgical access device of claim 7, wherein the first portion of each spiral segment of the plurality of spiral segments is slidable with respect to the second portion of the adjacent spiral segment of the plurality of spiral segments such that the conduit is in the first state.

9. The surgical access device of claim 8, wherein the first portion of each spiral segment of the plurality of spiral segments is fixed with respect to the second portion of the adjacent spiral segment of the plurality of spiral segments such that the conduit is in the second state.

10. The surgical access device of claim 1, wherein adjacent segments of the plurality of segments are interlocked.

11. A method of accessing a surgical site comprising:
positioning a tubular member of a surgical access device through an opening in tissue, the surgical access device having a valve assembly coupled to a housing, the valve assembly including a port attachable to a source of fluid;
guiding a distal portion of the tubular member toward a target site;
manipulating the tubular member to follow a predetermined path while the tubular member is in a first state, the tubular member including:
a proximal opening and a distal opening, an annular lumen defined between an inner wall and an outer wall, the annular lumen in fluid communication with the port, and a conduit including a passageway configured to receive a surgical instrument, the conduit extending along a length of the tubular member, the conduit disposed in the annular lumen and transitionable between a first state and a second state, the conduit including a plurality of spiral segments, each spiral segment of the plurality of spiral segments having a first section and a second section, the first section including a first flange and a first trough, the second section including a second flange and a second trough, the first flange being slidably disposed in the second trough and the second flange being slidably disposed in the first trough such that the spiral segments of the plurality of spiral segments are movable relative to one another such that the conduit has a flexible configuration in the first state and a fixed configuration in the second state; and removing fluid from the annular lumen thereby transitioning the tubular member from the first state to a second state wherein the tubular member is rigid.

12. The method of claim 11, wherein manipulating the tubular member includes manipulating a conduit disposed in the annular lumen of the tubular member.

13. The method of claim 12, wherein manipulating the conduit includes manipulating the plurality of spiral segments of the conduit such that the first section of one spiral segment of the plurality of spiral segments slidably engages the second section of an adjacent spiral section of the plurality of spiral segments.

14. The method of claim 11, wherein removing fluid from the annular lumen causes the inner wall of the lumen and the outer wall of the lumen to contact surfaces of the spiral segments of the plurality of spiral segments of the conduit.

15. The method of claim 14, wherein removing fluid from the annular lumen causes the first sections to become fixed in relation to the second sections and defining the second state of the tubular member.

16. The method of claim 11, further including inserting a flexible surgical instrument through the tubular member while the tubular member is in the first state.

17. The method of claim 11, wherein removing fluid from the annular lumen includes operating the valve on the housing that is coupled to a proximal end of the tubular member.

18. The method of claim 11, further including:
introducing fluid into the annular lumen thereby transitioning the tubular member from the second state to the first state; and
removing the tubular member from the opening in tissue.

19. The method of claim 18, wherein introducing fluid into the annular lumen includes operating the valve on the housing that is coupled to a proximal end of the tubular member.

* * * * *